(12) United States Patent
Giudiceandrea

(10) Patent No.: US 8,973,626 B2
(45) Date of Patent: Mar. 10, 2015

(54) METHOD AND APPARATUS FOR DETECTING THE THREE-DIMENSIONAL STRUCTURE OF A LOG

(75) Inventor: Federico Giudiceandrea, Bressanone (IT)

(73) Assignee: Microtec S.R.L., Bressanone (IT)

(*) Notice: Subject to any disclaimer, the term of this patent is extended or adjusted under 35 U.S.C. 154(b) by 706 days.

(21) Appl. No.: 12/796,095

(22) Filed: Jun. 8, 2010

(65) Prior Publication Data

US 2010/0314002 A1 Dec. 16, 2010

(30) Foreign Application Priority Data

Jun. 11, 2009 (EP) .................................. 09425228
Feb. 11, 2010 (EP) .................................. 10153383

(51) Int. Cl.
| | |
|---|---|
| B23Q 16/00 | (2006.01) |
| G01B 11/25 | (2006.01) |
| B27B 1/00 | (2006.01) |
| B27B 31/04 | (2006.01) |
| B27B 31/06 | (2006.01) |
| G01N 33/46 | (2006.01) |

(52) U.S. Cl.
CPC .............. *G01B 11/2518* (2013.01); *B27B 1/00* (2013.01); *B27B 31/04* (2013.01); *B27B 31/06* (2013.01); *G01B 2210/52* (2013.01); *G01N 33/46* (2013.01)
USPC ............ 144/392; 144/397; 144/407; 144/414

(58) Field of Classification Search
USPC ......... 144/367, 369, 376, 378, 379, 387–389, 144/392, 397, 398, 403, 407, 408, 414, 416
See application file for complete search history.

(56) References Cited

U.S. PATENT DOCUMENTS

| | | | | |
|---|---|---|---|---|
| 3,456,700 A | * | 7/1969 | Ahlstedt | 144/357 |
| 3,513,321 A | * | 5/1970 | Sherman | 250/559.25 |
| 4,294,149 A | * | 10/1981 | Olsson | 83/435.21 |
| 5,257,101 A | | 10/1993 | Lee | |
| 5,421,385 A | * | 6/1995 | McGee | 144/357 |
| 5,538,056 A | * | 7/1996 | Thoma | 144/342 |
| 6,628,819 B1 | | 9/2003 | Huang et al. | |
| 7,046,838 B1 | | 5/2006 | Sakagawa et al. | |
| 2003/0071194 A1 | | 4/2003 | Mueller et al. | |
| 2004/0027347 A1 | | 2/2004 | Farsaie | |

FOREIGN PATENT DOCUMENTS

| | | |
|---|---|---|
| WO | 2008/027150 A2 | 3/2008 |
| WO | 2008/093375 A1 | 8/2008 |

* cited by examiner

*Primary Examiner* — Shelley Self
*Assistant Examiner* — Onekki Jolly
(74) *Attorney, Agent, or Firm* — Pearne & Gordon LLP

(57) ABSTRACT

A method for detecting the three-dimensional structure of a log comprises the operating steps of:
making the log (2) rotate axially, leaving it free to translate during the rotation;
during said rotation repeating the step of detecting the relative surface structure of the log (2) at least at one log surface portion (13), so that the relative surface structure of substantially all of the points of at least the log (2) lateral surface is detected at least once; and
combining the relative surface structures detected to reconstruct an overall surface structure for at least the log (2) lateral surface,
the detection steps being carried out in such a way that each detection step result shares at least several points with at least one other detection step result, while the step of combining the relative surface structures is carried out in such a way that the shared points are made to coincide with each other.

12 Claims, 4 Drawing Sheets

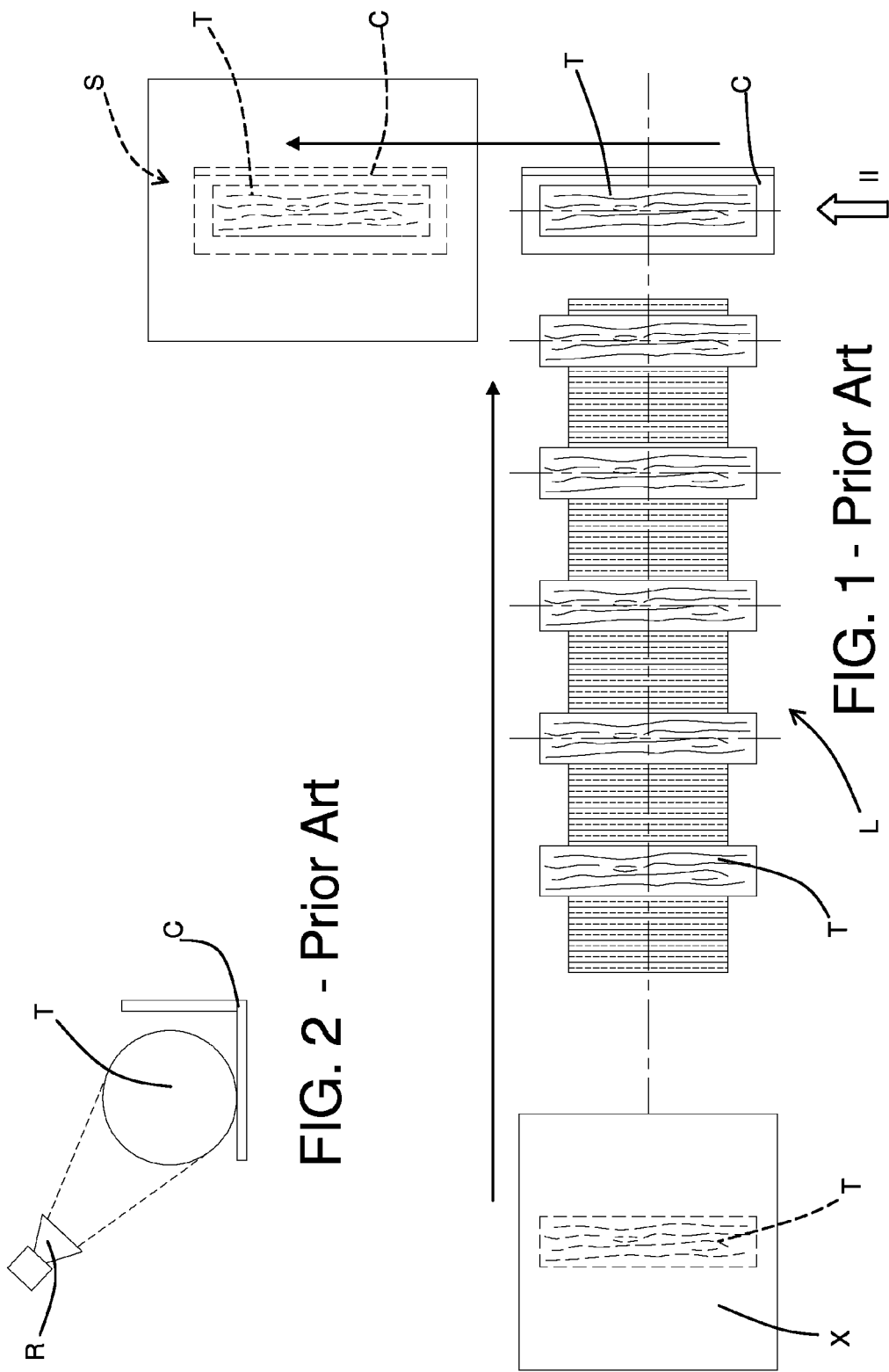

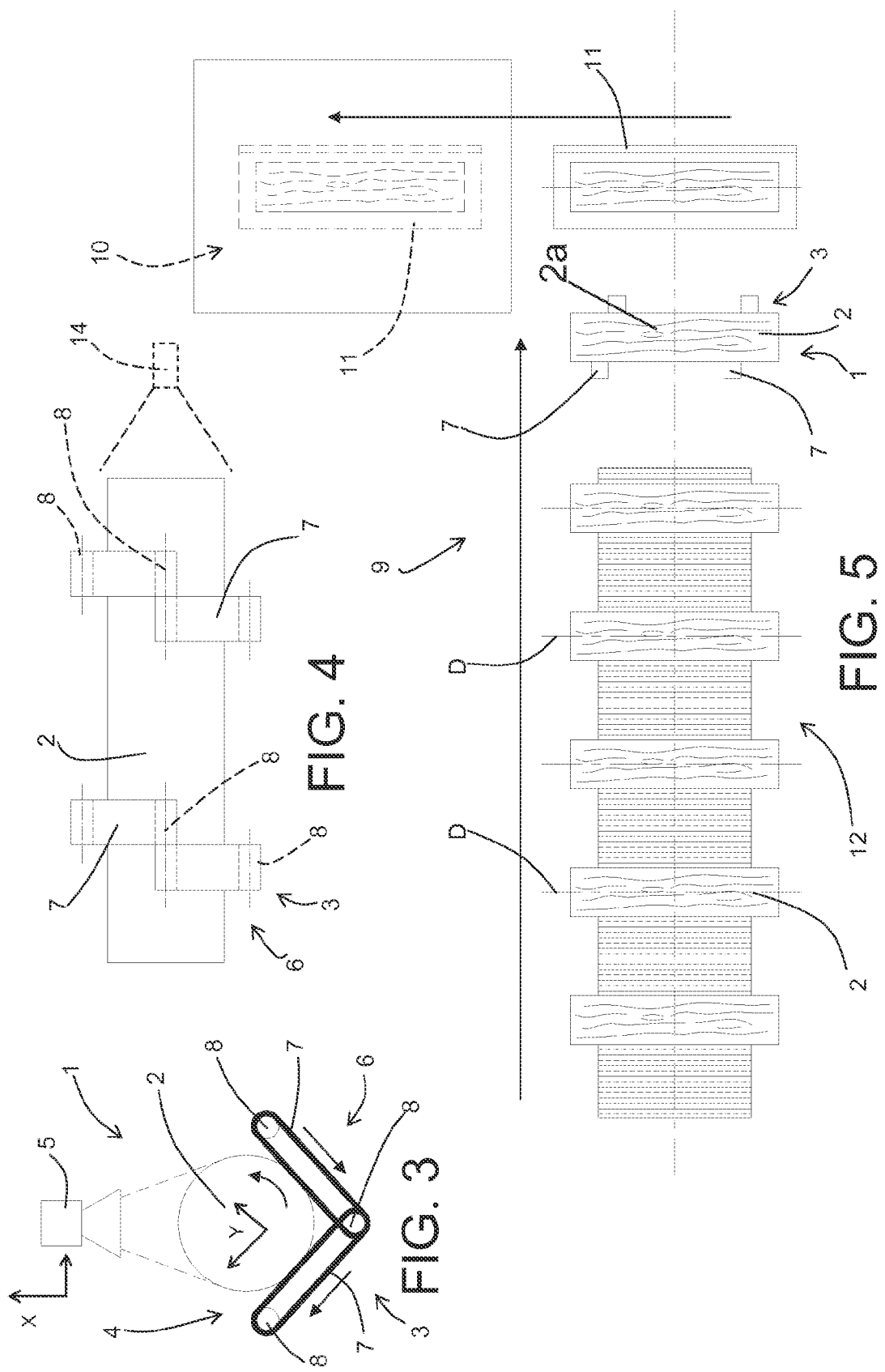

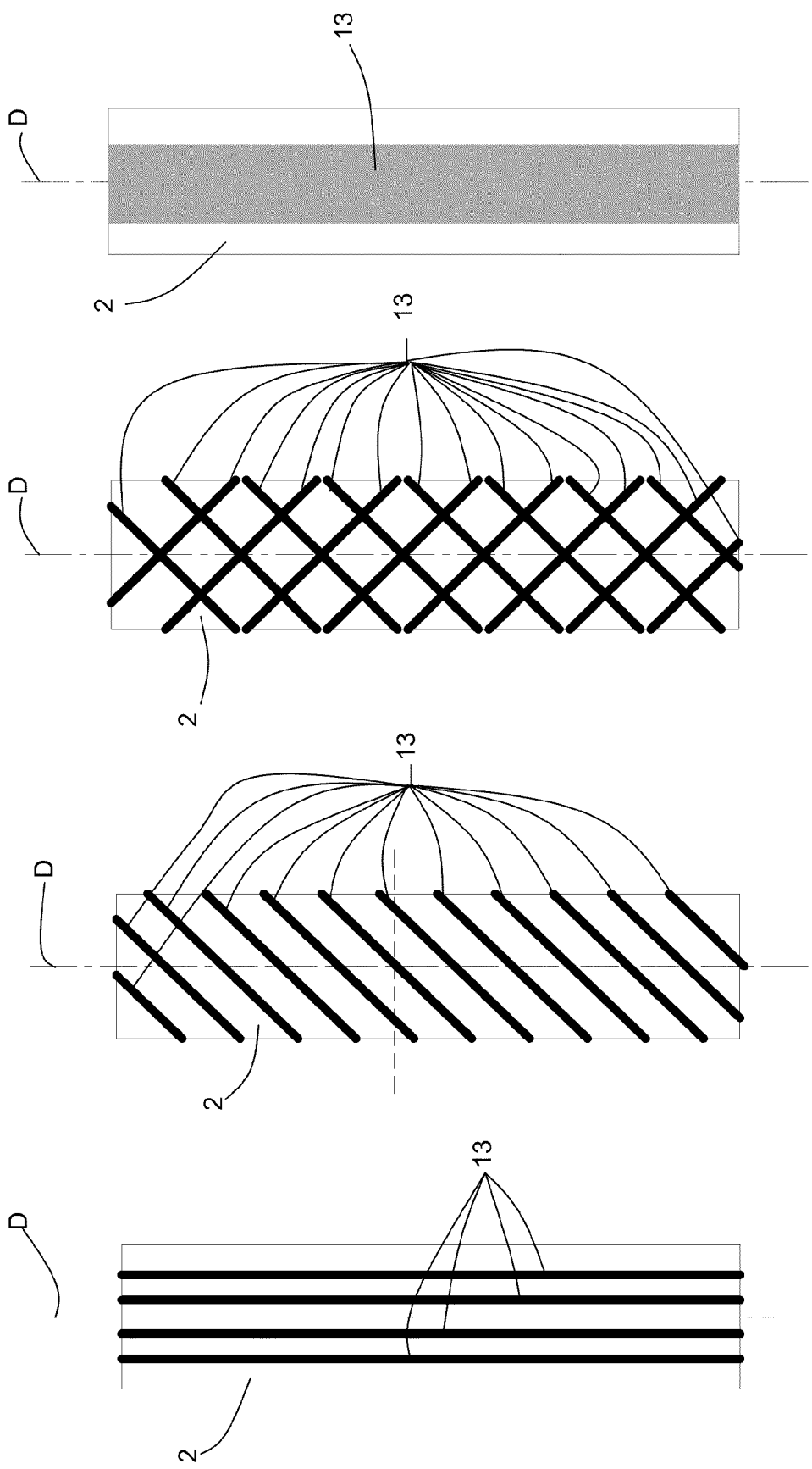

METHOD AND APPARATUS FOR DETECTING THE THREE-DIMENSIONAL STRUCTURE OF A LOG

The present invention relates to a method and an apparatus for detecting the three-dimensional structure of a log.

In particular, the present invention is advantageously applied in log cutting lines (FIG. 1), where the logs T are fed in sequence, positioned transversally to their direction of extension, to a band saw S. In more detail, a line L feeds one log T at a time to a movable carriage C which then moves it against the band saw S.

In plants of that type, cutting must be carried out in such a way as to optimise the result based on the characteristics of the log. To do that, the precise structure of the log must therefore be known.

According to a first known technology (schematically illustrated in FIG. 1), the log T is subjected to a three-dimensional scan upstream of the feed line. Therefore, in the station X, the three-dimensional structure of the log is detected and the control system can identify the best cutting pattern which can be applied. Consequently, when the log T arrives on the carriage C, only its position in space needs to be identified to allow correct application of the best cutting pattern previously identified.

However, that solution is relatively complicated to produce, since it requires a suitable detection station X in which the log must be stopped and observed on each side with suitable three-dimensional scanners.

Alternatively, the most widespread solution involves examination of the log T when it is already on the band saw S carriage C using a detector R. This solution is schematically illustrated in FIG. 2, which shows the portion of the plant indicated by the arrow II in FIG. 1. Obviously, in the solution in FIG. 2, the cutting plant does not comprise the scanning station upstream which in contrast is present in the solution in FIG. 1.

However, this latter solution also has disadvantages. Although it is simpler to produce, it has the significant limitation that the presence of the carriage C only allows examination of one side of the log T (as illustrated in FIG. 2). Consequently, the structure of the other side must be assumed.

Apart from the disadvantages of the apparatuses used in cutting plants which use band saws, it should be noticed that all prior art apparatuses of this type have disadvantages.

Apparatuses for detecting the three-dimensional structure of logs may be divided into two large families, those in which the log remains stationary, and those in which the log is fed along its main direction of extension.

In the former type of apparatuses, the main disadvantage is linked to the need to provide a large number of detection devices in order to be able to simultaneously detect the entire lateral surface of the log. Consequently, that type of apparatus is relatively expensive.

In contrast, in the latter case, the lateral surface is usually detected using cross-sections one after another as the log gradually passes through a detection station where two or more radial detectors detect each cross-section. In this latter case, the disadvantages are linked both to the need to provide two or more detectors (although smaller) and, above all, the fact that it is impossible to apply the technique to compact, high productivity production lines in which the logs must be fed positioned perpendicularly to the feed direction (if not rotating each log).

In this situation, the technical purpose which forms the basis of the present invention is to provide a method and an apparatus for detecting the three-dimensional structure of a log which overcome the above-mentioned disadvantages.

In particular, the present invention has for a technical purpose to provide a method and an apparatus for detecting the three-dimensional structure of a log which may be used in lines in which the log is fed positioned perpendicularly to its own direction of extension.

The present invention also has for a technical purpose to provide a method and an apparatus for detecting the three-dimensional structure of a log which allows the use of even a single detection device for detecting the entire lateral surface of the log.

The technical purpose specified and the aims indicated are substantially achieved by a method and an apparatus for detecting the three-dimensional structure of a log as described in the appended claims.

Further features and advantages of the present invention are more apparent in the detailed description below, with reference to several preferred, non-limiting embodiments of a method and an apparatus for detecting the three-dimensional structure of a log, described with reference to the accompanying drawings, in which:

FIG. 1 is a schematic plan view of a log cutting plant made according to the prior art;

FIG. 2 is a detail of a different log cutting plant made according to the prior art;

FIG. 3 is a front view of an apparatus for detecting the three-dimensional structure of a log made according to the present invention;

FIG. 4 is a bottom view of the apparatus of FIG. 3;

FIG. 5 illustrates a log cutting plant equipped with an apparatus for detecting the three-dimensional structure of a log made according to the present invention;

FIG. 6 illustrates a first embodiment of a detecting step which is part of the method according to the present invention;

FIG. 7 illustrates a second embodiment of a detecting step which is part of the method according to the present invention;

FIG. 8 illustrates a third embodiment of a detecting step which is part of the method according to the present invention;

FIG. 9 illustrates a fourth embodiment of a detecting step which is part of the method according to the present invention;

Figure 11:
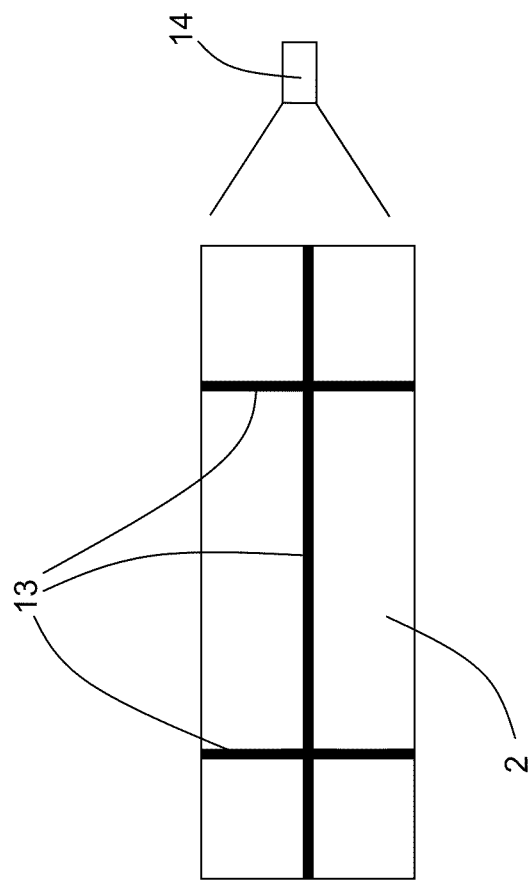
FIG. 11 illustrates a sixth embodiment of a detecting step which is part of the method according to the present invention.

With reference to the accompanying drawings, the numeral 1 denotes as a whole an apparatus for detecting the three-dimensional structure of a log 2 in accordance with the present invention.

The apparatus 1 comprises firstly supporting means 3 forming a holder 4 for a log 2 to be examined and means 5 for detecting the log 2 lateral surface structure which are pointing towards the holder 4.

In more detail, the supporting means 3 also form means 6 for making the log 2 rotate about two or more axes of rotation (described in more detail below) which are substantially parallel with the log 2 main direction of extension D. In the preferred embodiment, this is achieved by making the supporting means 3 with at least one pair of motor-driven supporting chains 7 angled at the two sides of the holder 4 and converging below it (in front view).

As shown in FIG. 3, the pair of supporting chains 7 therefore form V-shaped supports. However, in other embodiments, the chains 7 which form each pair may also be spaced out, and they may or may not form a V shape when seen from the front. In the embodiment illustrated, the supporting means 3 comprise two pairs of chains 7, but in general they may comprise a plurality of them distributed along the length of the holder 4 to support the log 2 at several points.

The supporting chains 7 are looped around respective feed/return rollers 8 and, as illustrated in FIG. 3, may be driven in a synchronised fashion and in the same direction to make the log 2 rotate. In FIG. 3 the log 2 is schematically illustrated as a circle, therefore after rotation of the chains 7 it is rotated about an axis of rotation passing through the centre of the circle. In contrast, in real conditions, the log 2 has an irregular cross-section, meaning that depending on the portion of the section resting on each chain 7, the instantaneous axis of rotation varies, although it always remains substantially parallel with the log 2 main axis of extension (except for small angles due to the different irregularity, such as irregularity or bump 2a in FIG. 5, of the individual sections resting on the support means 3 at each moment).

It shall be understood that in other embodiments the supporting and rotating means 3 may be made differently to what is described above.

According to the present invention, the detection means 5 are positioned on only one side of the holder 4 (above it in FIG. 3) so that they can always see only one part of the lateral surface of the log 2. Depending on requirements, the detection means 5 may have any structure. In particular, according to what is also described below, the detection means 5 may be means for detecting by laser triangulation, by detecting the texture of the surface of the log 2, etc. Moreover, the control and processing means are operatively connected to the detection means 5 for controlling their activation, for receiving detection step results from them and for reconstructing the log 2 overall surface structure, according to the methods described below. The control and processing means are also operatively connected to the means 6 for making the log rotate, to control their operation.

In order to be able to detect the entire lateral surface of the log 2, the control and processing means are programmed to carry out the operating steps of the method forming the subject matter of the present invention described in detail below. However, very briefly, the control and processing means are programmed to detect the entire lateral surface of the log 2 in a plurality of steps one after another, during each of which only a portion of the surface is detected. However, each portion detected is detected in such a way that it is at least partly superposed on at least one other portion detected, or to be detected, so that the overall surface may be reconstructed by superposing the individual portions which were individually detected.

In a more complete embodiment, the apparatus 1 may comprise one or more detectors 14 which are positioned in such a way that they can detect one or both of the log 2 end surfaces, and operatively connected to the control and processing means for operating according to the methods indicated in detail below. However, to summarise, it may be said that in this case the control and processing means are programmed to activate the detectors 14 simultaneously with the detection means 5 at least for a plurality of lateral surface detection steps, so as to provide an overall detection step result consisting of the portion of lateral surface and one or both end surfaces. If this is done for all of the lateral surface detection steps, it is not necessary for the lateral portions detected to be partly superposed, since the end surfaces always are. Consequently, the reconstructions can be performed entirely or partly based on the information relating to the end surfaces.

Before examining the method according to this invention in detail, it must be emphasised that the present invention also relates to a log 2 cutting plant 9 comprising a band saw 10, a carriage 11 for supporting a log 2 to be cut and able to move between a first, pick up position where a log 2 can be loaded on the carriage, and a second, cutting position where the band saw 10 can cut a log 2 positioned on the carriage, and a line 12 for feeding logs 2 to be cut to the carriage 11 located in the pick up position. According to the present invention, the plant 9 also comprises an apparatus 1 for detecting the three-dimensional structure of the log 2 made according to what is described above and preferably positioned downstream of the feed line 12. In particular, the apparatus 1 may either be positioned between the feed line 12 and the carriage 11 to form a kind of loader for the carriage 11, or it may be mounted directly on the carriage 11 (or may even form the carriage 11 itself).

If the apparatus 1 is an integral part of a log cutting plant 9, there may also advantageously be means for positioning the log 2 in the optimum cutting position (not illustrated). Said means are controlled by the control and processing means and are designed to position the log 2 on the carriage 11 in the optimum cutting position decided in the meantime, according to known methods, by the control and processing means, after the log 2 has been completely detected. In particular, when the apparatus 1 is mounted directly on the carriage 11, or coincides with it, the apparatus also forms the positioning means. In contrast, when the apparatus 1 is located directly upstream of the carriage, the positioning means may be either devices able to transfer the log 2 from the apparatus 1 to the carriage 11 with a predetermined rigid motion (such as a robot), or, more simply means for applying on the log 2 a visual positioning reference (such as a diametral line on an end face of the log 2). In the latter case, correct log cutting positioning is determined by the operator who rotates the log 2 to align the visual reference relative to a predetermined orientation (for example vertical). The method according to the present invention generally comprises firstly the operating step of making the log 2 rotate about two or more axes of rotation which are substantially parallel with the log main direction of extension D. In practice, that depends, as already indicated, on the methods used to carry out the step (for example, depending on the structure and operation of the apparatus 1 supporting means 3 as described above).

Secondly, during said rotation, the method involves detecting the relative surface structure of the log 2 at least at one lateral surface portion 13. The term "relative" surface structure refers to a reference system outside the log 2 (in practice usually integral with the detection means 5).

It should be noticed that if two reference systems are assigned, the first Y to the detection means 5 and the second X to the log 2, after log 2 rotation the first reference system Y integral with it may, relative to the second system Y, be subject to not just a rotation, but also a series of translations, for example after the irregularity of its surface which gradually rests on the supporting means 3 described above.

Also, according to a first embodiment of this invention the detection step is repeated a plurality of times, thus detecting at least once the relative surface structure of substantially all of the points of the lateral surface of the log 2, and, at the same time, so that, at the end of all of the repetitions, each surface portion 13 detected shares at least several points with at least one other surface portion 13 detected. It should be noticed that the term surface portion 13 refers to a set of real points of the surface of the log 2, whilst the term relative surface structure refers to detection of the surface trend of a predetermined surface portion 13.

The final basic step of the method disclosed involves combining the relative surface structures detected to reconstruct an overall surface structure for the log 2, and in particular combining them so that the points shared by the various relative surface structures are made to coincide with each other.

In the preferred embodiment of the method according to the invention, the detection steps are repeated in such a way that during each detection step points of the lateral surface of the log 2 are detected which are adjacent to those detected during the previous detection step. In this way, the entire lateral surface of the log 2 can be detected during a single log 2 rotation over itself.

Any methods may be used for carrying out the detection steps and they are not described in detail here, being of the known type. However, in the preferred embodiments, the detection steps are generally carried out by projecting a beam of light (preferably laser) on the surface of the log 2 and practically instantly detecting the surface structure of the illuminated zone using the triangulation technique. In contrast, in other embodiments, detection is carried out by detecting the log 2 surface texture (that is to say, its outer appearance). It is known that the three-dimensional appearance of an irregular object can be reconstructed according to how the appearance of the same zone of the surface of the object varies with variations in the reciprocal positioning between the point of observation (detection) and the zone of the surface detected. In other embodiments, the log surface can also be detected using the "time of flight" technique, in which the position of the surface points is obtained by measuring the time taken by a light pulse to reach the log and return to a detection sensor (this technique is of the known type and therefore not described in detail). Advantageously, to check the entire surface of the log rotary mirrors may be used, combined with interferometric techniques.

FIGS. 6 to 10 show five possible embodiments for each detection step (with reference to the positioning of FIG. 3, FIGS. 6 to 11 show a top view of the log 2) according to the first embodiment of the method disclosed, described here. In general, each portion 13 detected consists of the set of linear intersections between the surface of the log 2 and a plurality of separate planes incident on it (in the accompanying drawings all of the planes are perpendicular to the drawing plane, but in general they could also be at an angle to it). In particular, in the case of FIGS. 6 and 7 the separate planes are parallel with each other and, respectively, substantially parallel with the log 2 main direction of extension D, and at an angle to it. Whilst in the former case each point of each portion 13 is detected a number of times equal to the number of parallel planes (four in FIG. 6), in the latter case the distance between the different planes and the relative angle relative to the axis of the log 2 must be such that for each intersection at least several points can be detected during a subsequent detection step. In FIG. 7 that situation is shown by the dashed line which shows how each point at it is detected during three separate detection steps.

In contrast, in the case in FIG. 8, the portion 13 of the lateral surface of the log 2 detected consists of the linear intersection between the surface and a second plurality of separate planes which are at an angle both to the surface and to each other. The second plurality of planes may be divided into a first group and a second group of parallel planes, the planes of the first group being at an angle to the planes of the second group. In this way the portion 13 detected forms a grid and all of the surface points are detected more than once.

In the case in FIG. 9, the detection planes are positioned side by side so that each surface portion 13 is a longitudinal band of the log 2 surface.

Figure 10:
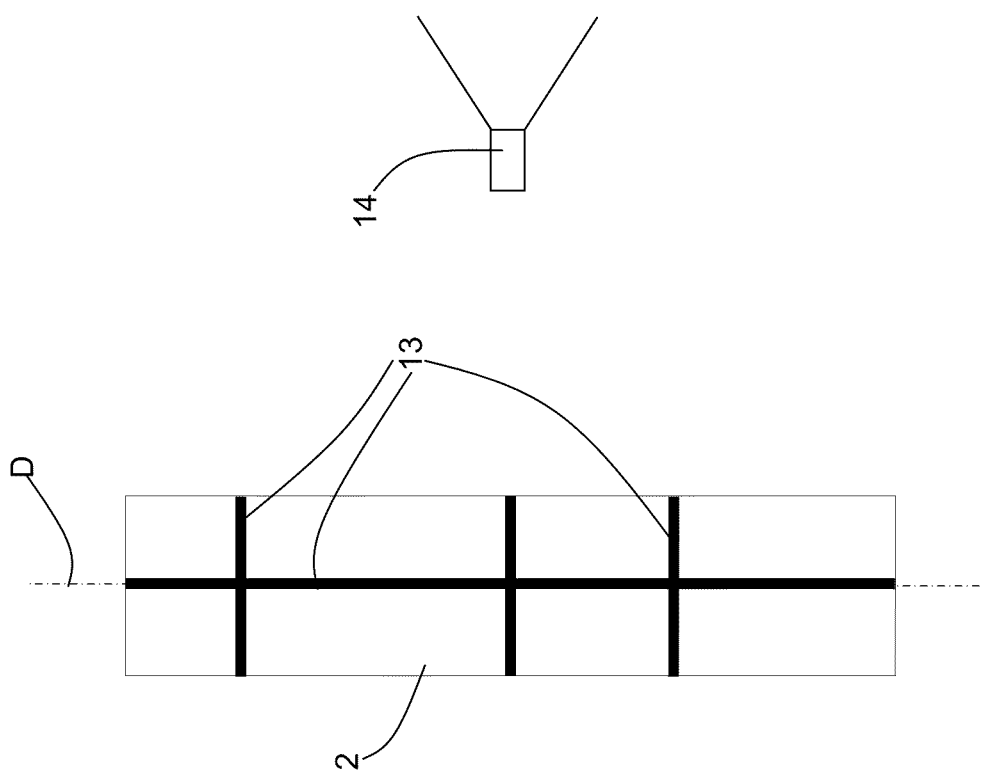
FIG. 10 illustrates a fifth embodiment of a detecting step which is part of the method according to the present invention.

Finally, in the case in FIG. 10, the portion 13 of the log 2 lateral surface detected consists of the linear intersection between the surface itself and one or more first planes substantially parallel with the main direction of extension (D) of the log (2) (or at least positioned in such a way that they cover the entire length of the log) and one or more second planes substantially perpendicular to the main direction of extension (D) of the log (2). In this way, each second plane always covers the same log circumference and, with each detection step, half of its is acquired, which can easily be superposed on the half detected during the next acquisition, from which it differs only by several points.

Returning to the step of making the log 2 rotate, it should also be noticed that this is preferably carried out with a substantially constant speed and in such a way that after a complete rotation the log 2 is substantially in the starting absolute position in space. As indicated, this may advantageously be achieved by supporting the log 2 using means 6 for making it rotate, such as those illustrated in FIGS. 3 and 4.

Moreover, advantageously, all of the detection steps are carried out by observing the log 2 from the same absolute position relative to the means 6 for making it rotate.

Finally, the step of combining the relative surface structures may be implemented by taking the results of one detection step as the starting point and referring all of the others to it. In particular, once the starting relative structure has been set (and therefore the corresponding starting surface portion 13), it is possible to superpose on it the other relative structures corresponding to the surface portions 13 sharing points with the starting surface portion 13, making the shared points coincide. In other words, a first reference system integral with the starting relative surface structure is set and the coordinates of all of the other relative surface structures are transformed into coordinates belonging to said first reference system. Experts in the field will not have any difficulty determining the transformation formulas to be applied by means of a comparison of the various relative surface structures detected.

In a more complex embodiment, the method according to the present invention may also comprise an additional operating step of observing at least one end face of the log 2, as illustrated in FIGS. 4 and 11 (where the face is observed by a suitable detector 14).

Advantageously, the end surface detection steps are associated with at least several of the relative surface structure detection steps. Preferably, the method disclosed may involve, simultaneously with at least a plurality of log 2 relative surface structure detection steps (advantageously all of them), the operating step of detecting at least one log end surface (preferably both). Advantageously, to detect the end surfaces the technique linked to the texture described above is preferably used.

Since the appearance of the end surface is usually well defined, knowledge of it simplifies reconstruction of the log 1 overall lateral surface.

According to the method of implementation described here, the step of combining relative surface structures is also carried out based on a comparison of the end surfaces that were detected at all or several of the relative surface structures. This is because a comparison of the different orientations in space detected for the same end surface allows one to infer the movement performed by the log even between the two steps for detecting the corresponding relative surface structures.

In particular, since the whole of the end surface is advantageously detected, a comparison between two subsequent detection step results reveals both the rotation to which the end surface was subjected and any translation of the end surface transversally to the axis of rotation. This addition to the first embodiment is particularly advantageous in the case of lateral surfaces which are too regular and which therefore do not provide sufficient references for correctly superposing the various detection step results, or, in the opposite case of surfaces that are too ragged and irregular and so produce a lot of "noise" in the detection step results.

The second preferred embodiment of the method according to this invention differs from the first embodiment described above only in the fact that one or both of the end surfaces is detected for each relative surface structure detection step, and the fact that there is no need for each relative surface structure (referred to the log 2 lateral surface) to share parts with the others. The detection step is in fact repeated in such a way that at least several points are shared by the results of two detection steps of one or both end surfaces of the log which have been carried out simultaneously with two corresponding detection steps for the relative surface structures. The reconstruction is performed exclusively based on superposing the end surfaces gradually detected. However, preferably, for a more accurate assessment of the log 2, it is preferable to observe both end surfaces, since the combination of their movements allows five of the six degrees of freedom of the log to be described. The only degree of freedom which cannot be obtained is the log movement along its main axis of extension (that is to say, perpendicularly to the end surfaces).

However, that information can be obtained by means of the detection steps on the lateral surface, by assessing where the log 2 ends. But in general, log movements in this direction are relatively rare.

The present invention brings important advantages. First, the method and the apparatus for detecting the three-dimensional structure of a log according to the present invention may be used in lines in which the log is fed positioned perpendicularly to its own direction of extension.

Secondly, they also allow the use of a single detection device for detecting the entire lateral surface of the log, during of a single rotation of the log.

Also, the present invention may be inserted in log cutting plants which use a band saw, in particular between the log feed line and the cutting carriage. It should also be noticed that the present invention is relatively easy to produce and even the cost linked to implementation of the invention is not very high.

The invention described above may be modified and adapted in several ways without thereby departing from the scope of the inventive concept.

All details of the invention may be substituted by other technically equivalent elements and, in practice, all of the materials used, as well as the shapes and dimensions of the various components, may vary according to requirements.

The invention claimed is:

1. A method for detecting the three-dimensional structure of a log, the log having a main direction of extension (D), the log having a lateral surface and two end surfaces, the lateral surface having irregularities, the lateral surface having a structure which is defined by a plurality of points, the lateral surface comprising a plurality of lateral surface portions (13), each lateral surface portion (13) having a structure which is defined by a group of said points;

the method comprising the steps of:
making the log (2) rotate;
during said rotation, in a first detection step, detecting, using detection means (5), a location, relative to the location of at least one other point detected in the first detection step, of each point of the group of points which define the structure of a first lateral surface portion (13),
repeating the detection step a plurality of times, and each time detecting, using detection means (5), a location, relative to the location of at least one other point detected in the same detection step, of each point of the group of points which define the structure of an additional lateral surface portion (13), at the end of the repetition substantially all of the points which define the structure of the lateral surface of the log having been detected at least once; and
combining the locations of said substantially all of the points to reconstruct an overall surface structure of at least the lateral surface of the log (2);
the method being characterized in that
the log (2) is made to rotate about two or more axes of rotation which are substantially parallel with the log's main direction of extension (D);
the step of making the log (2) rotate is carried out by resting the lateral surface of the log (2) on means (6) for making the log rotate, so that the instantaneous axis of rotation varies depending on which portions of the lateral surface of the log are resting on the rotation means (6), due to the irregularities of the lateral surface;
wherein (a) each structure of a lateral surface portion (13) detected shares several points with at least one other structure of a lateral surface portion (13) detected, and/or (b) at least two additional detection steps are performed, each additional detection step comprising detecting one or both end surfaces of the log simultaneously with a corresponding detection step of the structure of a lateral surface portion (13), wherein several points are shared by the results of the at least two additional detection steps; and
wherein the step of combining the locations is carried out in such a way that (a) the points shared by two different detected structures of lateral surface portions (13) are made to coincide if each of the two detected structures of a lateral surface portion (13) shares several points with the other detected structure of a lateral surface portion (13), and/or (b) the end surfaces detected in two additional detection steps simultaneously with the structures of two lateral surface portions (13) are made to coincide if several points are shared by the results of said two additional detection steps.

2. The method according to claim 1, wherein repeating the detection step a plurality of times is performed in such a way that during each such detection step locations of points are detected which are adjacent to locations of points detected during the immediately previous detection step.

3. The method according to claim 1, wherein repeating the detection step a plurality of times is performed in such a way as to detect the entire lateral surface structure of the log (2) during a single 360° rotation of the log (2).

4. The method according to claim 1, characterized in that during each detection step a lateral surface portion (13) is detected which consists of the linear intersection between the lateral surface of the log (2) and at least one plane incident to the lateral surface of the log (2).

5. The method according to claim 4, characterized in that during each detection step a lateral surface portion (13) is detected which consists of the linear intersection between the lateral surface of the log (2) and a plurality of separate planes incident on the lateral surface of the log (2).

6. The method according to claim 5, characterized in that during each detection step a lateral surface portion (13) is detected which consists of:
- the linear intersection between the lateral surface of the log (2) and a first plurality of separate planes which are parallel or substantially parallel with the log (2) main direction of extension (D), or at an angle to the log (2) main direction of extension (D); or
- the linear intersection between the lateral surface of the log (2) and a second plurality of separate planes which are at an angle to the lateral surface of the log (2) and which are grouped in a first group and a second group of parallel planes, the planes of the first group being at an angle to the planes of the second group; or
- the linear intersection between the lateral surface of the log (2) and at least one first plane which is substantially parallel with the log (2) main direction of extension (D) and at least one second plane which is substantially perpendicular to the log (2) main direction of extension (D).

7. The method according to claim 1, characterized in that the step of making the log (2) rotate is carried out with a substantially constant speed.

8. The method according to claim 1, characterized in that the step of making the log (2) rotate is carried out in such a way that after a complete rotation the log (2) is substantially in the same starting absolute position in space.

9. The method according to claim 8, characterized in that the step of making the log (2) rotate is carried out by supporting the log (2) with means (6) for making the log rotate and also being characterized in that all of the detection steps are carried out while detecting the log (2) from the same absolute position relative to the means (6) for making the log rotate.

10. The method according to claim 1, characterized in that an additional detection step of also detecting at least one end surface of the log is performed simultaneously with each of the detection steps of the structure of a lateral surface portion (13), the step of combining the locations also being carried out or only being carried out in such a way that the end surfaces detected in each additional detection step simultaneously with the structures of corresponding lateral surface portions (13) are made to coincide.

11. The method according to claim 1, characterized in that the combining step includes taking one detection step result as a starting point and gradually superposing on said one detection step result the other detection step results which share points with said one detection step result.

12. The method according to claim 10, characterized in that the combining step includes taking one detection step result as a starting point and gradually superposing on said one detection step result the other detection step results.

* * * * *